(12) United States Patent
Kim et al.

(10) Patent No.: US 10,709,754 B2
(45) Date of Patent: Jul. 14, 2020

(54) **COMPOSITION FOR PREVENTING, AMELIORATING, OR TREATING HYPERURICEMIA OR METABOLIC DISORDERS RELATED WITH HYPERURICEMIA COMPRISING EXTRACT OF *ALPINIA OXYPHYLLA* AS EFFECTIVE INGREDIENT**

(71) Applicant: KOREA INSTITUTE OF ORIENTAL MEDICINE, Daejeon (KR)

(72) Inventors: Dong Seon Kim, Daejeon (KR); Ohn Soon Kim, Daejeon (KR); Yun Mi Lee, Daejeon (KR); Young-Sil Lee, Daejeon (KR); Eun Jung Son, Sejong-si (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 39 days.

(21) Appl. No.: 16/086,672

(22) PCT Filed: Apr. 7, 2017

(86) PCT No.: PCT/KR2017/003808
§ 371 (c)(1),
(2) Date: Sep. 20, 2018

(87) PCT Pub. No.: WO2017/176082
PCT Pub. Date: Oct. 12, 2017

(65) Prior Publication Data
US 2019/0099465 A1 Apr. 4, 2019

(30) Foreign Application Priority Data
Apr. 8, 2016 (KR) .................. 10-2016-0043548

(51) Int. Cl.
*A61K 36/9068* (2006.01)
*A61K 36/9062* (2006.01)
*A23L 33/105* (2016.01)
*A61P 19/06* (2006.01)
*A61K 45/06* (2006.01)

(52) U.S. Cl.
CPC ........ *A61K 36/9062* (2013.01); *A23L 33/105* (2016.08); *A61K 45/06* (2013.01); *A61P 19/06* (2018.01); *A23V 2002/00* (2013.01); *A23V 2200/30* (2013.01); *A23V 2250/21* (2013.01); *A61K 2236/331* (2013.01)

(58) Field of Classification Search
CPC ................................. A61K 36/9068

USPC ......................................... 424/756
See application file for complete search history.

(56) References Cited

U.S. PATENT DOCUMENTS

2004/0102524 A1* 5/2004 Hughes .................. A61K 31/00
514/651
2007/0243132 A1 10/2007 Russell-Jones et al.

FOREIGN PATENT DOCUMENTS

| CN | 103518915 A | * | 1/2014 |
|---|---|---|---|
| JP | 2002-121145 A | | 4/2002 |
| JP | 2002121145 A | * | 4/2002 |
| KR | 1992-0011502 A | | 7/1993 |
| KR | 10-2006-0120791 A | | 11/2006 |
| KR | 10-2010-0073818 A | | 7/2010 |
| KR | 10-2013-0026376 A | | 3/2013 |
| KR | 10-1567885 B1 | | 11/2015 |

OTHER PUBLICATIONS

International Search Report for PCT/KR2017/003808.
Morikawa T. et al., "Absolute Stereostructures of Three New Sesquiterpenes from the Fruit of Alpinia Oxyphyl La with Inhibitory Effects on Nitric Oxide Production and Degranulation in RBL-2H3 Cells", Journal of Natural Products, vol. 65, No. 10, 30, pp. 1468-1474, 2002.
Yoon Jae-Hong, "Professor Yoon Jae-Hong's Pain Manual for Each Body Part", Medical Hani; Korean-oriental portal site, Sep. 14, 2018 (machine translation is submitted herewith.).

* cited by examiner

Primary Examiner — Michael Barker
Assistant Examiner — Deborah A Davis
(74) Attorney, Agent, or Firm — The PL Law Group, PLLC

(57) ABSTRACT

The present invention relates to a composition for preventing, ameliorating, or treating hyperuricemia or metabolic disorders related with hyperuricemia comprising an extract of *Alpinia oxyphylla* as an effective ingredient. Because the extract of *Alpinia oxyphylla* of the present invention can reduce the uric acid amount in blood of an animal model and is derived from natural products, and the raw materials can be easily obtained, it can be widely used in industries that are related to hyperuricemia or metabolic disorders related with hyperuricemia. It can be effectively used for prevention, amelioration, or treatment of gout or gouty arthritis, in particular.

16 Claims, 4 Drawing Sheets

COMPOSITION FOR PREVENTING, AMELIORATING, OR TREATING HYPERURICEMIA OR METABOLIC DISORDERS RELATED WITH HYPERURICEMIA COMPRISING EXTRACT OF *ALPINIA OXYPHYLLA* AS EFFECTIVE INGREDIENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/003808, filed Apr. 7, 2017, which claims priority to the benefit of Korean Patent Application No. 10-2016-0043548 filed in the Korean Intellectual Property Office on Apr. 8, 2016, the entire contents of which are incorporated herein by reference.

TECHNICAL FIELD

The present invention relates to a composition for preventing, ameliorating, or treating hyperuricemia or metabolic disorders related with hyperuricemia comprising an extract of *Alpinia oxyphylla* as an effective ingredient.

BACKGROUND ART

Hyperuricemia is defined by blood uric acid value of more than 6.8 to 7.0 mg/dl in men or more than 6.0 mg/dl in women. In the United State, approximately 3 million to 5 million people suffer from hyperuricemia and metabolism disorders related with hyperuricemia (e.g., gout). The possibility of having gout by African Americans is two times the Caucasians in the United States. Gout and hyperuricemia are also very widely spread in China, Japan, Polynesian countries, and Sub-Saharan Africa. Between 1990 and 2010, occurrence rate of gout has increased by 2 times, and number of the gout patient tends to increase by 14% on average per year in South Korea.

Examples of the metabolism disorders related with hyperuricemia include not only gout but also uric acid crystals, precipitation of uric acid crystals in joint, acute monoarticular arthritis caused by precipitation of uric acid crystals in kidney tissues, pain crisis of inflammatory arthritis, urinary tract stone, renal stone, and gouty nephropathy. Chronic renal stone and gouty nephropathy are known to increase the risk of having kidney damage and renal failure. Among the metabolic disorders related with hyperuricemia, gout is a disease by which, in accordance with increased concentration of uric acid in blood (i.e., waste product of purine which has been taken from foods, i.e., waste product of the metabolism by human body), uric acid salts are precipitated in cartilage, tendon, or peripheral tissues (i.e., in blood, body fluid, and joint fluid, uric acid is present in the form of uric acid salts). Those phenomena cause joint inflammation to yield a recurrent crisis accompanying severe pain, and, according to precipitation of gouty tophi resulting from uric acid crystals, a deformation and a damage in joint are yielded. Other than the problems in joint, various renal disorders are also caused and nephrolithiasis (i.e., lithonephria) by which stones are formed inside a kidney due to the uric acid may be caused.

Furthermore, gout is exhibited with steps like asymptomatic hyperuricemia, acute gouty arthritis, interval gout, chronic tophaceous gout, and the like. The asymptomatic hyperuricemia which appears at an early stage indicates a state in which, although there is an increase in blood uric acid concentration, symptoms like arthritis, gouty tophi, and uric acid nephrolithiasis are not exhibited yet. Acute gouty arthritis is a stage in which, after hyperuricemia which generally continues at least for 20 years, a gouty crisis or nephrolithiasis occurs. The most characteristic symptom is acute crisis of very painful arthritis. At an early stage, a single joint may be invaded without having a systemic symptom, but, more and more joints may be gradually invaded along with high fever. The interval gout indicates a period in which there is no symptom between gouty crises. In most cases, the second crisis occurs between 6 months and 2 years after having the first crisis. Although it may vary depending on the treatment, frequency of the crisis gradually increases, thus yielding invasion into many joints. Chronic tophaceous gout is similarly shown like other arthritis once the symptom is developed to a chronic tophaceous gout stage after the interval period having no gout. Gradual stiffness and continuous pain occur in an invaded joint.

Although gout is known as a disorder which has a clearly established therapy and can be successfully cured, as there are many cases in which it is accompanied with other disorders like high blood pressure and chronic renal failure, careful consideration regarding side effects of pharmaceuticals is often needed, and, as a non-pharmaceutical treatment, efforts of a patient to change his lifestyle are essential for having favorable prognosis of a long-term treatment. Gout and hyperuricemia show clinical conditions like high blood pressure, hyperlipidemia, increased blood sugar level, abdominal obesity, or the like, and although they do not fall into the category of diagnosis standards of metabolic syndrome, which is complex conditions that can bring increased risk of having an adult disease like arteriosclerotic heart disease and type 2 diabetes, they are believed to have a close relationship with a metabolic syndrome. It has been reported that 44% of the gout patients in South Korea also have a metabolic syndrome. Although gout is generally exhibited in the form of acute monoarthritis, a few joints may be invaded, or, in rare case, several joints are invaded by gout. It is well known that non-steroidal anti-inflammatory drugs (NSAIDs), which are used for a treatment of acute gout, can suppress an inflammatory response. Both colchicines and steroids, which exhibit an anti-inflammatory activity by suppressing the activity and movement of white blood cells, are a pharmaceutical that can effectively treat gout crisis. It is known that a selective cyclooxygenase (COX-2) inhibitor also has the same effect as existing NSAIDs.

Furthermore, if the blood uric acid concentration is maintained at saturation state or lower level for a long period of time, not only the acute gouty arthritis can be prevented but also the size of previously-formed gouty tophi can be reduced. For a treatment of lowering the blood uric acid concentration at chronic stage of gout, two main kinds of a uric acid lowering agent are used, i.e., xanthine oxidase (XO) inhibitor and uricosuric agent. As for an inhibitor for uric acid synthesis, there is allopurinol which has been conventionally used and febuxostat which has been recently developed as a new pharmaceutical. Allopurinol is an XO inhibitor which can be effectively used regardless of the cause of hyperuricemia. However, the most significant side effect of allopurinol is hypersensitivity syndrome, and, with exhibition of high fever, erythema, increased eosinophils, hepatitis, renal failure or the like, it is known to have a risk of causing death. Febuxostat is also an oxidase inhibitor, but, unlike allopurinol, it is mainly metabolized in liver as a non-purine-based selective blocker, and generates glucuronide. Most gout cases progress into chronic gout, and for those cases, an anti-inflammatory preparation and a treatment of reducing uric acid concentration are given as a preventive measure even when there is no symptom. The preventive treatment should be carried out only after the disease is maintained in a moderate state for a certain period of time. If not, gout may recur in more severe form. However, the suitable moderate period of disease is still controversial, and suppressing an abrupt onset of gout, which recurs intermittently, by a preventive treatment cannot be achieved with pharmaceuticals which have been developed until now. In addition, the technique for inhibiting the oxidase as a gout-inducing enzyme by using natural products remains insufficient at present moment.

Meanwhile, *Alpinia oxyphylla* is a fruit of Zingiberaceae, and it naturally grows in Haenamsung and Kawndong area in China. *Alpinia oxyphylla* has both ends with slightly sharp globular or elliptical shape with length of 1 to 2 cm and diameter of 7 to 10 mm. The outside has brown to dark brown color and has several small bump-like protruded lines that are longitudinally connected to each other. Thickness of the fruit skin is 0.3 to 0.5 mm, and as the fruit skin is tightly adhered to a seed lump, it is difficult to peel the skin. Inside of the fruit is divided into three sections by thin membrane, and 5 to 8 seeds, which adhere to one another via a pseudo seed coat, are present in each section. The seed has brown to dark brown color, and, as an irregular polyhedron, it has diameter of about 3.5 mm and hard texture. It has unique smell and slightly bitter taste. As known components of *Alpinia oxyphylla*, it is believed that nootkatone, epinootkatol, β-nootkatol, β-pinene, p-cymene, terpinen-4-ol, yakuchinone A and B, which are a diarylheptanoid compound, and tectochrysin, chrysin, izalpinin, and 3,5-dihydroxy-7,4'-dimethoxyflavone as a flavonoid component are contained. Nootkatone has an anti-stomach ulcer activity, and yakuchinone A and B have an anti-inflammation activity and can suppress an occurrence of skin cancer and lower the expression of COX-2 and iNOS and the activity of NFκB. Other than those, it is also known that yakuchinone A, nootkatone, and epinootkatol have an insecticidal effect, and they are also known to exhibit an activity of protecting brain cells, an anti-allergy activity, a skin whitening activity, or the like.

It is also known that essential oil components of *Alpinia oxyphylla* can increase the skin permeability of pharmaceuticals, exhibit an activity of relaxing smooth muscle and suppressing cardiac muscle by suppressing competitively the introduction of calcium ions into a cell, and also have an anti-diuretic activity, an anti-ulcer activity, an anti-dementia activity, and an activity of improving learning abilities.

As a technique relating to an extract of *Alpinia oxyphylla* or hyperuricemia, a method and a composition for treating hyperuricemia and a disorder related with hyperuricemia is described in Korean Patent Registration No. 1567885. In Korean Patent Application Publication No. 2006-0120791, a pharmaceutical composition for improving lipid metabolism and preventing and treating obesity comprising an extract of *Alpinia oxyphylla* is disclosed. In Korean Patent Application Publication No. 1992-0011502, an improved oriental therapeutic material of Bujaeejoongtang for treating pains of a human neural system is disclosed.

However, the composition for preventing, ameliorating, or treating hyperuricemia or metabolic disorders related with hyperuricemia of the present invention, which comprises an extract of *Alpinia oxyphylla* as an effective ingredient, has not been disclosed.

SUMMARY

The present invention is devised under the circumstances described above, and according to the present invention, a composition for preventing, ameliorating, or treating hyperuricemia or metabolic disorders related with hyperuricemia comprising an extract of *Alpinia oxyphylla* as an effective ingredient is provided. Furthermore, by confirming that the extract of *Alpinia oxyphylla* as an effective ingredient of the present invention can reduce uric acid in blood, the present invention is completed accordingly.

To achieve the object described above, the present invention provides a functional health food for preventing or ameliorating hyperuricemia or metabolic disorders related with hyperuricemia comprising an extract of *Alpinia oxyphylla* as an effective ingredient.

The present invention further provides a pharmaceutical composition for preventing or treating hyperuricemia or metabolic disorders related with hyperuricemia comprising an extract of *Alpinia oxyphylla* as an effective ingredient.

The present invention relates to a composition for preventing, ameliorating, or treating hyperuricemia or metabolic disorders related with hyperuricemia comprising an extract of *Alpinia oxyphylla* as an effective ingredient. Because it can reduce the uric acid amount in blood and is derived from natural products, and raw materials of the composition can be easily obtained, it can be widely used in industries that are related to hyperuricemia or metabolic disorders related with hyperuricemia. It can be effectively used for prevention, amelioration, or treatment of gout or gouty arthritis, in particular.

DETAILED DESCRIPTION

Figure 1:
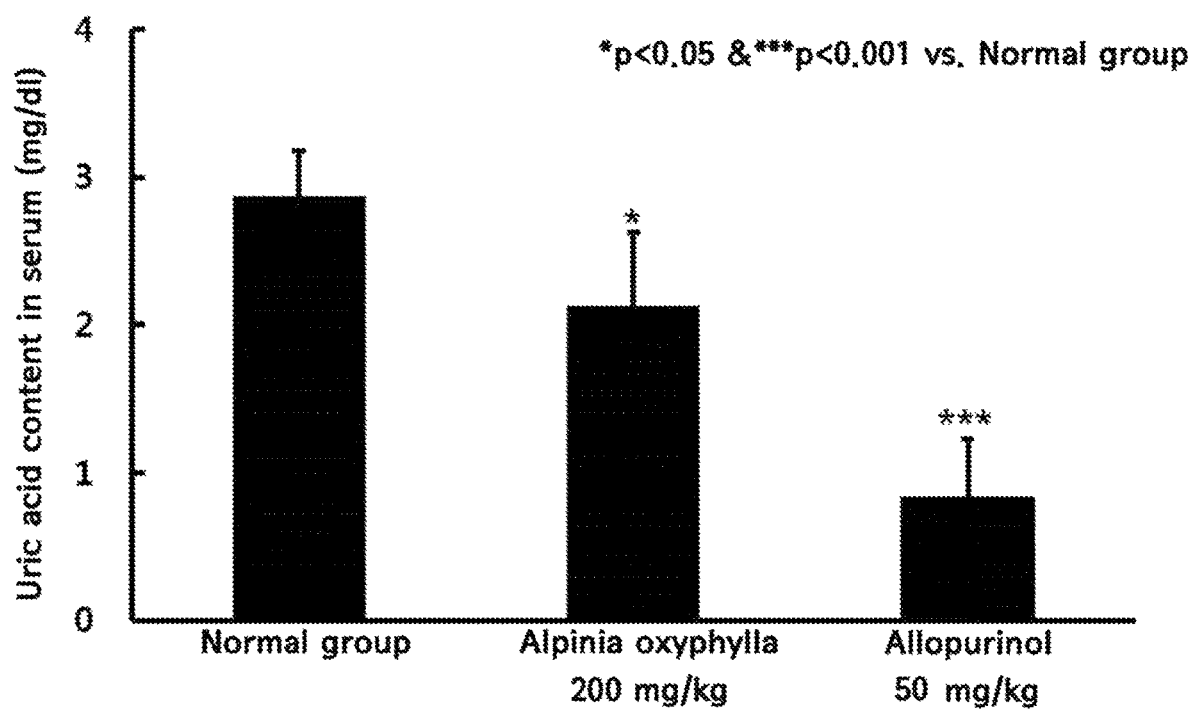
FIG. 1 shows the result of determining the decrease in uric acid amount in serum after administering the extract of *Alpinia oxyphylla* of the present invention to a normal SD-rat animal model. The normal group indicates a normal animal model group, and *Alpinia oxyphylla* 200 mg/kg indicates an animal model group in which 200 mg/kg of the extract of *Alpinia oxyphylla* are administered to a normal animal model group.

The present invention relates to a functional health food for preventing or ameliorating hyperuricemia or metabolic disorders related with hyperuricemia comprising an extract of *Alpinia oxyphylla* as an effective ingredient.

The metabolic disorders related with hyperuricemia are preferably any one selected from acute or chronic gout, gouty flare, gouty arthritis, gouty kidney stone, and gouty nephropathy, but it is not limited thereto. The gouty flare means a symptom showing redness or the like which is caused by inflammation due to gout.

It is preferable that the extract of *Alpinia oxyphylla* is extracted by using $C_1$-$C_4$ lower alcohol, water, or a mixture thereof as a solvent. It is more preferably extracted by using ethanol as a solvent. It is even more preferably extracted by using 70% (v/v) ethanol as a solvent, but it is not limited thereto.

The functional health food for preventing or ameliorating hyperuricemia or metabolic disorders related with hyperuricemia comprising an extract of *Alpinia oxyphylla* as an effective ingredient can be prepared in any form selected from a drink, a pill, a tablet, a capsule, and a powder preparation. It may be also prepared by addition to other food products or food components, and it can be suitably prepared according to a general method.

As for an example of the food products to which the extract of *Alpinia oxyphylla* of the present invention can be added, it can be any one selected from meats, sausages, breads, chocolates, candies, snacks, cookies, pizza, ramen, other noodles, gums, dairy products including ice cream, various soups, beverages, tea, drinks, alcohol beverages, and vitamin complexes, and it includes any health food products in general sense.

The functional health food may further comprise various nutritional supplements, a vitamin, a mineral (electrolyte), an artificial and natural flavor, a coloring agent, an enhancing agent (e.g., cheese, chocolate, or the like), pectinic acid and a salt thereof, alginic acid and a salt thereof, an organic acid, protective colloidal thickening agent, a pH adjusting agent, a stabilizer, a preservative, glycerin, alcohol, and a carbonating agent used for carbonated drink. Other than those, fruit flesh for producing natural fruit juice or vegetable drink can be also comprised. Those components may be used either independently or in combination thereof.

The functional health food of the present invention may further comprise various flavors or natural carbohydrates as an additional component. Examples of the natural carbohydrates include monosaccharides such as glucose or fructose, disaccharides such as maltose or sucrose, polysaccharides such as dextrin or cyclodextrin, and sugar alcohols such as xylitol, sorbitol, or erythritol. As a sweetening agent, a natural sweetening agent such as thaumatin or stevia extract and a synthetic sweetening agent such as saccharine or aspartame can be used.

The present invention also relates to a pharmaceutical composition for preventing or treating hyperuricemia or metabolic disorders related with hyperuricemia comprising an extract of *Alpinia oxyphylla* as an effective ingredient.

With regard to the pharmaceutical composition, the metabolic disorders related with hyperuricemia are preferably any one selected from acute or chronic gout, gouty flare, gouty arthritis, gouty kidney stone, and gouty nephropathy, but it is not limited thereto. The gouty flare means a symptom showing redness or the like that is caused by inflammation due to gout.

Other than the effective ingredient described above, uric acid salt-lowering agent may be further comprised. It is preferable that the uric acid salt-lowering agent is at least one selected from xanthine oxidase inhibitor, uricosuric agent, uric acid salt oxidase, urine alkalinizing agent, and fenofibrate, but it is not limited thereto. Other than the extract of *Alpinia oxyphylla*, a pharmaceutically acceptable carrier, vehicle, or diluent may be further comprised.

The pharmaceutical composition of the present invention may be prepared in various formulations including an oral formulation and a parenteral formulation. In case of producing a preparation, production is made by using a diluent or a vehicle such as filler, bulking agent, binding agent, moisturizing agent, disintegrating agent, or surfactant that are commonly used for producing a preparation. As for the solid preparation for oral administration, a tablet, a pill, a powder preparation, a granule, a capsule or the like are included, and such solid preparation is produced by mixing at least one compound with one or more vehicles such as starch, calcium carbonate, sucrose, lactose, or gelatin. Furthermore, other than simple vehicles, a lubricating agent such as magnesium stearate or talc can be also used. As for the liquid preparation for oral administration, a suspension, a solution preparation for internal use, an emulsion, a syrup preparation, or the like can be mentioned. Other than water or liquid paraffin as a commonly used simple diluent, various kinds of a vehicle such as moisturizing agent, sweetening agent, aromatic agent, or preservatives may be included. Examples of a preparation for parenteral administration include a sterilized aqueous solution, a non-aqueous preparation, a suspension, an emulsion, a freeze-dried preparation, and a suppository. As a water insoluble solvent or a suspending agent, propylene glycol, polyethylene glycol, or vegetable oil such as olive oil, and injectable ester such as ethylolate can be used. As a base for a suppository, witepsol, macrogol, tween 61, cacao fat, laurin fat, glycerol, gelatin, or the like can be used.

The composition of the present invention can be administered either orally or parenterally. In case of parenteral administration, it is preferable to choose external application on skin, intraperitoneal, rectal, intravenous, muscular, subcutaneous, endometrium injection, or intracerebroventricular injection. Most preferably, the composition is used for external application on skin.

The composition of the present invention is administered in a pharmaceutically effective amount. As described herein, the expression "pharmaceutically effective amount" means an amount sufficient for treating a disorder at reasonable benefit-risk ratio that can be applied for a medical treatment. The effective dose level may be determined based on a type or severeness of a disorder of a patient, activity of a pharmaceutical, sensitivity to a pharmaceutical, administration period, administration route, excretion ratio, time period for therapy, elements including a pharmaceutical used in combination, and other elements that are well known in the medical field. The composition of the present invention can be administered as a separate therapeutic agent, or it can be administered in combination with other therapeutic agent. It can be administered in order or simultaneously with a conventional therapeutic agent. It can be also administered as single-dose or multi-dose. It is important to administer an amount which allows obtainment of the maximum effect with minimum dose while considering all of the aforementioned elements without having any side effect, and the dosage can be easily determined by a person skilled in the pertinent art.

The dosage of the composition of the present invention may vary depending on bodyweight, age, sex, health state, diet of a patient, administration period, administration method, excretion rate, and severeness of disorder.

Hereinbelow, the present invention is explained in greater detail in view of the Examples. However, the following Examples are given only for specific explanation of the present invention and it wound be evident to a person who has common knowledge in the pertinent art that the scope of the present invention is not limited by them.

EXAMPLES

Example 1. Preparation of Extract of *Alpinia oxyphylla*

To 1 kg of *Alpinia oxyphylla*, 15 l of 70% (v/v) ethanol were added, and, after reflux extraction for 3 hours at 85, the filtered solution was concentrated under reduced pressure at 50° C. followed by drying to obtain 11.7 g of an extract of *Alpinia oxyphylla*.

Example 2. Determination of Reduced Uric Acid Contained in Blood in Normal SD-rat Animal Model Each of 200 mg/kg extract of *Alpinia oxyphylla* and 50 mg/kg allopurinol as a positive control was suspended in 0.01 M PBS (phosphate buffered saline) containing 0.1% polyoxyethylene sorbitan monooleate, and orally administered once to a SD-rat, which is a normal animal model.

Two hours after the oral administration, the animal was anesthetized with ethyl ether, and blood was taken from the animal. By using a uric acid assay kit (AB65344, ABCAM, USA), the uric acid amount was measured.

As it is illustrated in FIG. 1, the result of measuring uric acid in blood was shown to be about 2.1 mg/dl, as a result of having a decreased uric acid amount according to an administration of the extract of *Alpinia oxyphylla*. It was confirmed that the uric acid in blood was reduced by 26% compared to the normal group.

Example 3. Analysis of Effect of Reducing Uric Acid Contained in Blood of Hyperuricemia-Induced Animal Model In order to induce hyperuricemia in a SD-rat, which is an animal model for inducing hyperuricemia, 150 mg/kg potassium oxonate that has been dissolved in 0.5% sodium carboxymethylcellulose (CMC-Na) solution (pH 5.0) containing 0.1 M sodium acetate was intraperitoneally injected to an animal.

Twenty-four hours later, urine was collected from the animal, and by using a uric acid assay kit (AB65344, ABCAM, USA), the animal model induced to have hyperuricemia was selected.

The extract of *Alpinia oxyphylla* at 100, 200, or 300 mg/kg and allopurinol at 50 mg/kg as a positive control group were suspended in 0.01 M PBS (phosphate buffered saline) containing 0.1% polyoxyethylene sorbitan monooleate, and the resultant was orally administered to the selected animals for 3 days. The animals were fasted for 16 hours before autopsy.

Two hours after the last oral administration, the animal was anesthetized with ethyl ether, and blood was taken from the animal. By using a uric acid assay kit (AB65344, ABCAM, USA), the uric acid amount was measured.

Figure 2:
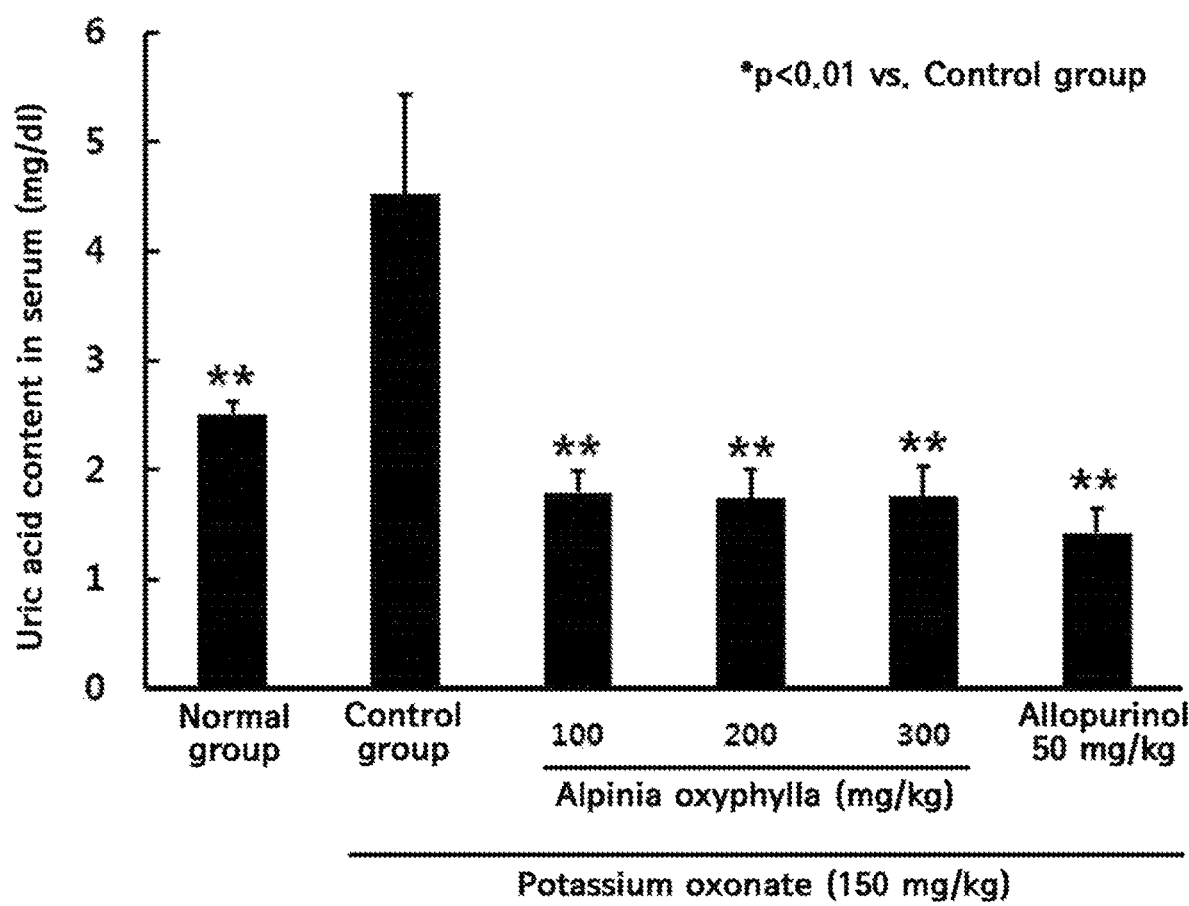
FIG. 2 shows the result of determining the decrease in uric acid amount in serum after administering the extract of *Alpinia oxyphylla* of the present invention to a SD-rat animal model with induced hyperuricemia. The normal group indicates a normal animal model group, and the control group indicates an animal model group in which potassium oxonate is administered to induce hyperuricemia.

The result of measuring the uric acid amount was shown to be increased to about 4.5 mg/dl in accordance with the administration of potassium oxonate, as it is illustrated in FIG. 2. It is confirmed that, as a result of administering the extract of *Alpinia oxyphylla* of the present invention in an amount of 100 mg/kg/day, 200 mg/kg/day, or 300 mg/kg/day to the hyperuricemia-induced animal model, the uric acid amount in serum has decreased from about 4.5 mg/dl to about 1.79, 1.75, or 1.76 mg/dl. Namely, it is found that, compared to the hyperuricemia animal model group, there is an effect of reducing the uric acid amount in blood by 60 to 62% or so in the hyperuricemia animal model which has been administered with the extract of *Alpinia oxyphylla* of the present invention.

Example 4. Evaluation of Efficacy of Extract of *Alpinia oxyphylla* in Animal Model with Gouty Arthritis Induced by MSU (Monosodium urate)

(1) Measurement of percentage of bodyweight loading (%)

To determine the efficacy of the extract of *Alpinia oxyphylla*, which has been extracted in Example 1, against gouty arthritis, percentage of bodyweight loading (%) was calculated for an animal model having gouty arthritis which has been induced by MSU.

The extract of *Alpinia oxyphylla* at 150 or 300 mg/kg, which is dissolved in 0.5% CMS, was orally administered to a 7-week old C57/BL6 mouse. One hour after administering the extract of *Alpinia oxyphylla*, MSU in an amount of 4 mg was suspended in 500 of PBS containing 2.5% tween and injected to right paw tissues of the animal to induce gouty arthritis. After administering the pharmaceutical once a day for 4 days, autopsy was carried out on Day 5 after the MSU induction. As a positive control, colchicine was used.

The percentage of bodyweight loading on hind paws was measured by using a device for measuring paw weight. Because the mouse with induced gouty arthritis relies on his healthy paws (i.e., paws not administered with any MSU) to stand up due to the pains, balance in weight is disrupted between two paws. Thus, according to the measurement, the weight of the paw administered with MSU was relatively lighter than the weight of the healthy paw. By using the measured paw weight (g), the percentage of bodyweight loading (%) was calculated. The percentage of bodyweight loading (%) indicates the pressing force exhibited by paw for maintaining the posture, and in normal cases, weight distribution ratio (%) is 50% for both paws. However, as the pain increases, lower weight distribution ratio (%) is yielded.

Percentage of bodyweight loading (%)=(Weight of hind paw having induced arthritis/Weight of normal hind paw+ Weight of hind paw having induced arthritis)×100

Figure 3:
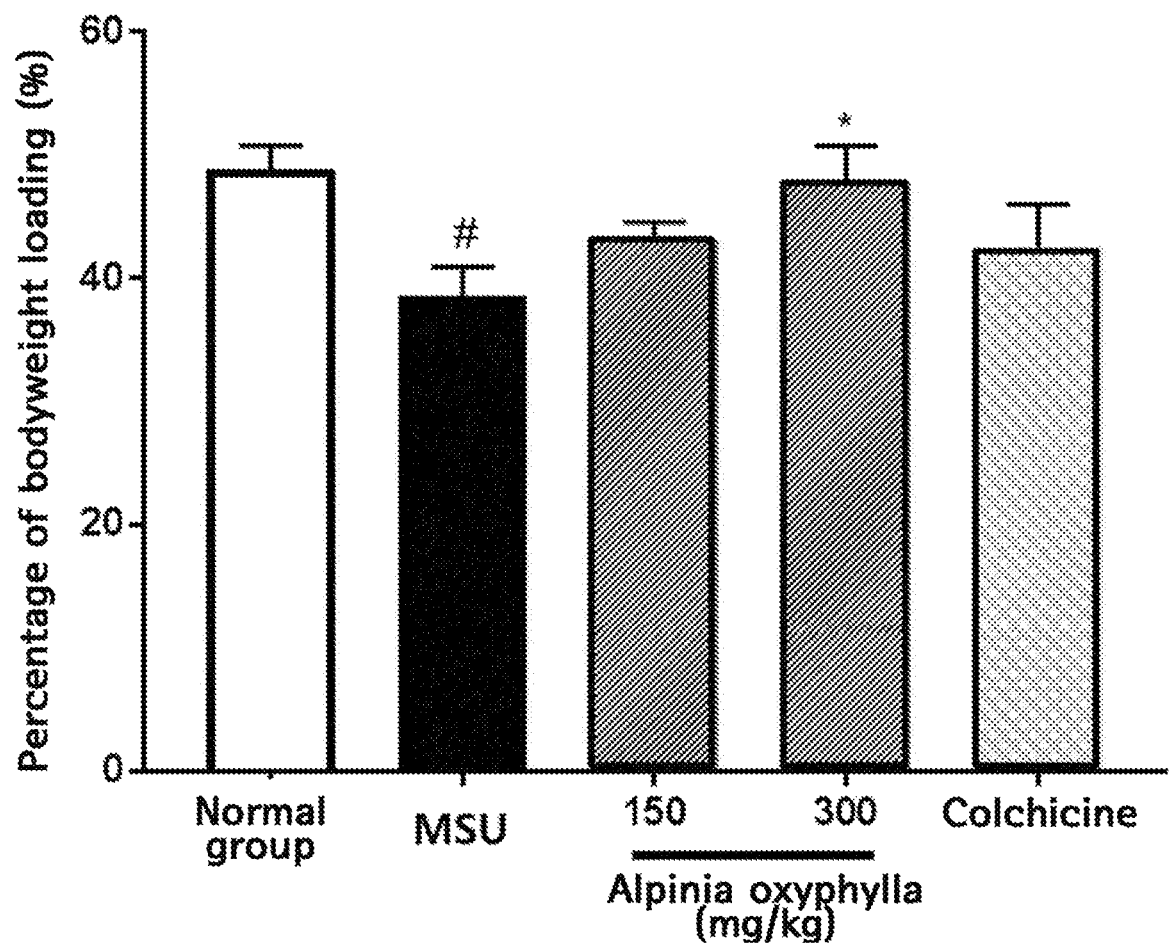
FIG. 3 shows the result of determining percentage of bodyweight loading (%) in C57/BL6 mouse which has been induced to have gouty arthritis by MSU (monosodium urate). The normal group is a negative control group, which is a normal group not induced to have gouty arthritis, MSU is a group induced to have gouty arthritis according to administration of MSU, and colchicines is a positive control group. # indicates that, compared to the normal group, the percentage of bodyweight loading (%) has decreased in statistically significant sense in the group which has been induced to have gouty arthritis according to administration of MSU and * means p<0.05. * indicates that, compared to the MSU group with induced gouty arthritis, the percentage of bodyweight loading (%) has increased in statistically significant sense in the group treated with the extract of *Alpinia oxyphylla* of the present invention, in which * means p<0.05.

As a result, the percentage of bodyweight loading is lower in MSU group compared to the normal group as it is illustrated in FIG. 3, and it was confirmed that the percentage of bodyweight loading is recovered in concentration dependent manner in the group which has been administered with the extract of *Alpinia oxyphylla* of the present invention.

(2) Determination of expression amount of IL-1β protein

To determine the efficacy of the extract of *Alpinia oxyphylla*, which has been extracted in Example 1, against gouty arthritis, an expression amount of IL-1β protein was analyzed for an animal model having gouty arthritis induced by MSU.

The extract of *Alpinia oxyphylla* at 150 or 300 mg/kg, which is dissolved in 0.5% CMS, was orally administered to a 7-week old C57/BL6 mouse. One hour after administering the extract of *Alpinia oxyphylla*, MSU in an amount of 4 mg was suspended in 500 of PBS containing 2.5% tween and injected to right paw tissues of the animal to induce gouty arthritis. After administering the pharmaceutical once a day for 4 days, autopsy was carried out on Day 5 after the MSU induction.

After that, paw tissues collected from the autopsy were added to RIPA buffer solution and dissociated, and then the expression amount of IL-1β protein, which is an inflammation indicator, in the supernatant of dissociated solution was measured by ELISA method. As a positive control, colchicine was used.

Figure 4:
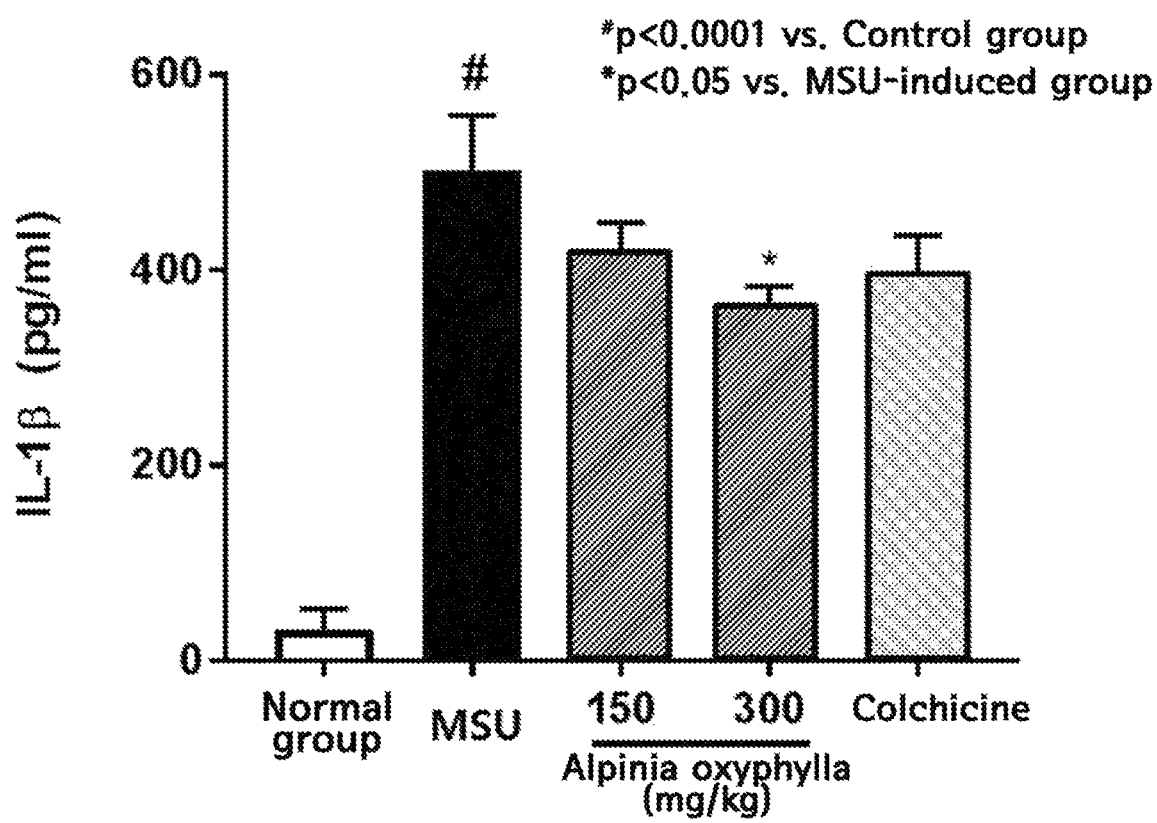
FIG. 4 shows the result of determining the effect of reducing IL-1β in C57/BL6 mouse which has been induced to have gouty arthritis by MSU. The normal group is a negative control group, which is a normal group not induced to have gouty arthritis, MSU is a group induced to have gouty arthritis according to administration of MSU, and colchicines is a positive control group. # indicates that, compared to the normal group, the content of IL-1β has increased in statistically significant sense in the group induced to have gouty arthritis according to administration of MSU, in which p<0.0001. * indicates that, compared to the MSU group with induced gouty arthritis, the content of IL-1β has decreased in statistically significant sense in the group treated with the extract of *Alpinia oxyphylla* of the present invention, in which * means p<0.05.

As a result, it was confirmed that IL-1β, which has increased due to gouty arthritis, decreases in significant sense according to the administration of the extract of *Alpinia oxyphylla*, as it is illustrated in FIG. 4.

What is claimed is:

1. A method for treating hyperuricemia or a metabolic disorder related with hyperuricemia, the method comprising administering to a subject in need thereof a composition comprising an extract of *Alpinia oxyphylla* as an effective ingredient,
wherein the extract of *Alpinia oxyphylla* is extracted by using ethanol as a solvent.

2. The method of claim 1, wherein the subject suffers from hyperuricemia.

3. The method of claim 1, wherein the subject suffers from the metabolic disorder related with hyperuricemia.

4. The method of claim 1, wherein the subject suffers from the metabolic disorder related with hyperuricemia selected from the group consisting of acute gout, chronic gout, gouty flare, gouty arthritis, gouty kidney stone, gouty nephropathy, and a combination thereof.

5. The method of claim 1, wherein the composition is included in a functional health food.

6. The method of claim 1, wherein the composition is a pharmaceutical composition.

7. The method of claim 6, wherein the pharmaceutical composition further comprises a uric acid salt-lowering agent.

8. The method of claim 7, wherein the uric acid salt-lowering agent is at least one selected from the group consisting of xanthine oxidase inhibitor, uricosuric agent, uric acid salt oxidase, urine alkalinizing agent, fenofibrate, and a combination thereof.

9. The method of claim 6, wherein the pharmaceutical composition further comprises a pharmaceutically acceptable carrier, vehicle, or diluent.

10. A method for treating hyperuricemia or a metabolic disorder related with hyperuricemia, the method comprising administering to a subject in need thereof an effective ingredient consisting of an extract of *Alpinia oxyphylla*.

11. The method of claim 10, wherein the subject suffers from hyperuricemia.

12. The method of claim 10, wherein the subject suffers from the metabolic disorder related with hyperuricemia.

13. The method of claim 10, wherein the subject suffers from the metabolic disorder related with hyperuricemia selected from the group consisting of acute gout, chronic gout, gouty flare, gouty arthritis, gouty kidney stone, gouty nephropathy, and a combination thereof.

14. The method of claim 10, wherein the extract of *Alpinia oxyphylla* is extracted by using ethanol.

15. The method of claim 10, wherein the effective ingredient is included in a functional health food.

16. The method of claim 10, wherein the effective ingredient is included in a pharmaceutical composition.

* * * * *